United States Patent [19]

Bonn et al.

[11] Patent Number: 5,585,236
[45] Date of Patent: Dec. 17, 1996

[54] NUCLEIC ACID SEPARATION ON ALKYLATED NONPOROUS POLYMER BEADS

[75] Inventors: Gunther Bonn, Zirl; Christian Huber, Rum, both of Austria; Peter Oefner, Palo Alto, Calif.

[73] Assignee: Sarasep, Inc., Santa Clara, Calif.

[21] Appl. No.: 153,046

[22] Filed: Nov. 17, 1993

[30] Foreign Application Priority Data

Nov. 18, 1992 [AT] Austria ..................... A2285/92

[51] Int. Cl.$^6$ ............ C12Q 1/70; C08F 112/08; C12N 15/00; B01D 15/08
[52] U.S. Cl. ............ 435/5; 435/6; 435/91.1; 435/91.2; 435/803; 210/656; 436/161; 536/23.1; 536/25.3; 526/347.2; 935/76; 935/77; 935/111
[58] Field of Search ............ 435/6, 803, 183; 436/161; 526/347.2; 935/76, 77, 111; 210/656; 536/23.1, 25.3

[56] References Cited

U.S. PATENT DOCUMENTS 4,563,510  1/1986  Ugelstad.

OTHER PUBLICATIONS

Journal Of Chromatography, (1990), 508:61–73, "Rapid High–Performance Liquid Chromatography of Nucleic Acids With Polystyrene–Based Micropellicular Anion Exchangers", MAA et al.

Nucleic Acids Research, (1993), 21:1061–1066, High–Resolution Liquid Chromatography Of DNA Fragments On Non–Porous Poly(Styrene–Divinylbenzene) Particles, Huber et al.

Journal Of Cromatography, (1992), 599:113–118, "High–Performance Liquid Chromatographic Separation Of Detritylated Oligonuceotides On Highly Cross–Linked Poly(Styrene–Divinylbenzene) Particles", Huber.

Journal Of Chromatography, (1986), 359:265–274, "Separation Of DNA Restriction Fragments By Ion–Pair Chromatography", Eriksson et al.

Analytical Biochemistry, (1985), 151:526–533, "Isolation Of Specific tRNAs Using An Ionic–Hydrophobic Mixed–Mode Chromatographic Matrix", Bischoff et al.

*Primary Examiner*—Stephanie W. Zitomer
*Assistant Examiner*—Bradley L. Sisson
*Attorney, Agent, or Firm*—William B. Walker

[57] ABSTRACT

Nonporous polymer beads having an average diameter of about 1–100 microns are suitable for chromatographic separation of mixtures of nucleic acids when the polymer beads are alkylated with alkyl chains having at least three carbon atoms. The polymer beads provide efficient separation of nucleic acids using ion-pair reverse phase chromatography.

35 Claims, 3 Drawing Sheets

NUCLEIC ACID SEPARATION ON ALKYLATED NONPOROUS POLYMER BEADS

BACKGROUND OF THE INVENTION

1. Field of the Invention

The present invention is directed to the separation of nucleic acids using nonporous polymeric beads. More specifically, the invention is directed to the chromatographic separation of both single strand and double strand nucleic acids by chromatography using chromatographic columns containing alkylated nonporous polymer beads.

2. Discussion of the Background

Nucleic acid separations have become a focus of scientific interest and numerous groups of researchers have been attempting to achieve improvements of various technical aspects in this area. Anion exchange separations together with ion pairing/reverse phase chromatography are among the most frequently used methodologies for the separation of nucleic acid species.

In European patent application (EP 0 507 591 A2), W. Bloch showed that, to a certain extent, a length relevant separation of DNA fragments was possible on nonporous anion exchangers with tetramethylammonium chloride (TMAC) containing eluents. However, as shown in FIG. 5 of this patent application, fragments with 458 and 504 base pairs (difference of 46 base pairs) elute at the same time and are not separated. Although, on the other hand it was possible to separate fragments differing only by 34 base pairs (fragments with 434 and 458 base pairs).

Additionally, an addition of TMAC causes a significant, general decrease in resolution. Also, because of the ion strength gradients necessary for achieving separations by Bloch's method and the resulting high nonvolatile salt concentrations, any subsequent examination and measurements on the separated fragments are not possible.

The method for separating DNA fragments on anion exchange materials, carrying trimethylammonium groups, reported by Y. Ohimya et al (Y. Ohimya et al, Anal. Biochem., (1990), 189:126–130) has the same drawbacks as the method utilizing anion exchangers with diethylaminoethyl groups for the separation of DNA fragments (Y. Kato et al, J. Chromatogr., (1989), 478:264). A separation strictly dependent on the size of DNA fragments is impossible in both cases. Furthermore, any subsequent measurements with the separated fractions are impossible due to high salt concentration of these fractions.

An important disadvantage of anion exchange separations of double stranded nucleic acids is the differing retention behavior of GC- and AT- base pairs. This effect makes a separation according to molecular size impossible. General utility of anion exchange for nucleic acid analyses is thus strongly reduced. Another important drawback of the anion exchange methodology is the necessity to use ionic strength gradients to achieve elution over the entire range of nucleic acid molecular weights. Strong contamination of eluting peak zones by salt, due to the ionic strength gradients, makes subsequent investigations of DNA molecule fractions very difficult.

There are also serious drawbacks with applications of reverse phase/ion pairing chromatography to separations of double stranded DNA fragments, at least with the current version of the procedure introduced by Eriksson et al. Most importantly, the relatively low separation efficiency of this methodology leads to insufficient resolution and to low recoveries for very short restriction fragments. Typical analytical run times with ion pairing/reverse phase chromatography are in the range of one to several hours (see S. Eriksson, G. Glad, P. A. Pernemalm, E. Westman J. Chromatogr, (1986), 359:265–274).

Some limited separations using nonporous polymeric packing beads were described by J. Thompson in Biochromatography, (1986), 1:16; (1986), 1:22; (1986), 1:68; (1987), 2:4).

Huber et al were the first to fully discuss the utilization of non-porous polystyrene beads as a stationary phase for reverse phase/ion pair chromatography. The disadvantages of the method used by Eriksson et al were thought to center around the use of porous silica beads for the reverse state stationary phase (C. G. Huber, P. J. Oefner and G. K. Bonn, J. Chromatogr., (1992), 599:113–118). Huber et al were able to show that separations of single stranded nucleic acids could indeed be improved by changing over from the silica based reverse phase material to nonporous polystyrene beads. Additional improvement was accomplished by inclusion of a polyvinyl alcohol into the polystyrene nonporous beads. Inclusion of polyvinyl alcohol was accomplished by addition during one of the synthetic steps of the procedure leading to the nonporous polymeric beads.

On the other hand, Huber et al were unable to achieve the same kind of improvement for the double stranded nucleic acids with their polymeric beads. More specifically, with the double stranded molecules, they observed an insufficient resolution for all analytes having more than 150 base pairs.

A need continues to exist for chromatographic methods for separating nucleic acids with improved separation efficiency and resolution.

SUMMARY OF THE INVENTION

Accordingly, one object of the present invention is to provide a chromatographic method for separating nucleic acids with improved separation and efficiency.

This and other objects which will become apparent from the following specification have been achieved by the method of the present invention in which nucleic acids are chromatographically separated using a separation column filled with alkylated nonporous polymeric beads.

DETAILED DESCRIPTION OF THE PREFERRED EMBODIMENTS

Figures 1A, 1B, 1C:
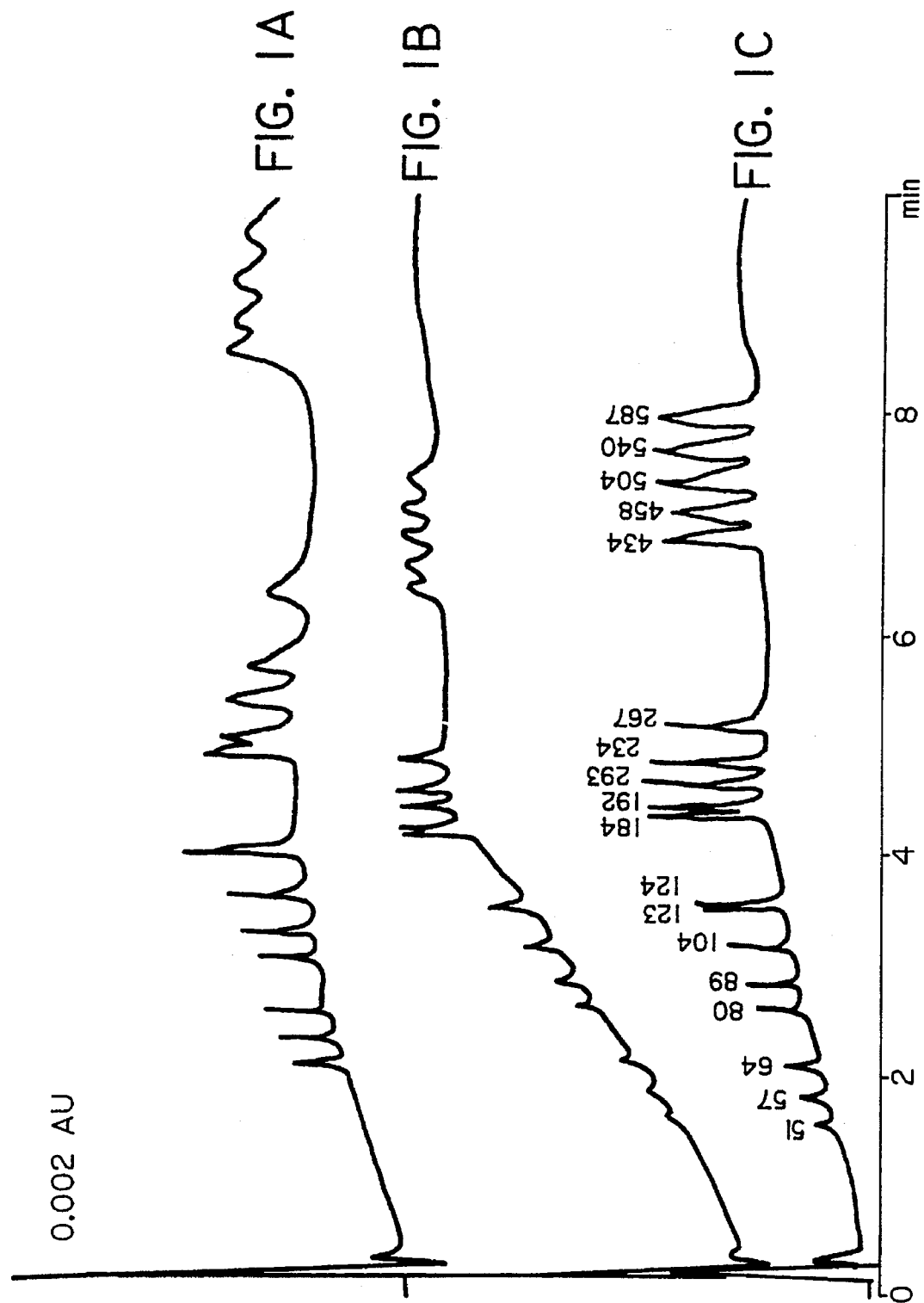
FIG. 1a is a chromatogram showing separation of DNA restriction fragments with a column filled with nonporous poly(ethylvinylbenzene-divinylbenzene) beads.
FIG. 1b is a chromatogram showing separation of the same DNA restriction fragments using a column filled with nonporous poly-(ethylvinylbenzene-divinylbenzene) beads treated with polyvinyl alcohol.
FIG. 1c is a chromatogram showing separation of the same DNA restriction fragments using alkylated nonporous poly(ethylvinylbenzene-divinylbenzene) beads of the present invention.

In its most general form, the subject matter of the present invention is the separation of nucleic acids with reverse phase ion pair chromatography (RPIPC) utilizing columns filled with nonporous polymeric beads having an average diameter of about 1–100 microns, preferably 1–10 microns, more preferably 1–5 microns. Beads having an average diameter of 1.5–3.0 microns are most preferred. Chromatographic efficiency of the column beads is predominantly influenced by the properties of surface and near-surface areas. For this reason, the following descriptions are related specifically to the close-to-the-surface region of the polymeric beads. The main body and/or the center of such beads may exhibit entirely different chemistries and sets of physical properties from those observed at or near the surface of the polymeric beads of the present invention.

The method of the present invention can be used to separate nucleic acids having up to about 1000 base pairs, although in most cases, the method will be used to separate nucleic acids having up to about 600 base pairs or fewer. The method provides good separation for longer nucleic acids having about 200–600 base pairs and also for short nucleic acids having only about 20–80 base pairs. The nucleic acids which may be separated by the present method include both single strand and double strand nucleic acids of DNA and RNA. Samples containing mixtures of nucleic acids may result from total synthesis of nucleic acids, cleavage of DNA or RNA with restriction endonucleases, as well as nucleic acid samples which have been multiplied and amplified using polymerase chain reaction techniques.

The nonporous polymeric beads of the present invention are prepared by a two step process in which small seed beads are initially produced by emulsion polymerization of suitable polymerizable monomers. The emulsion polymerization procedure of the invention is a modification of the procedure of Goodwin et al. (J. W. Goodwin, J. Hearn, C. C. Ho and R. H. Ottewill Colloid & Polymer Sci., (1974), 252:464–471). Monomers which may be used in the emulsion polymerization process to produce the seed beads include styrene, alkyl substituted styrenes, alpha-methyl styrene, and alkyl substituted alpha-methyl styrenes, preferably monomers where the benzene-type ring is substituted with 1–4 $C_{1-6}$ alkyl groups, and the monomers described, for example, in U.S. Pat. No. 4,563,510. This patent is incorporated herein by reference in its entirety. The seed polymer beads are then enlarged and alkylated to produce the nonporous polymeric beads of the present invention.

The seed beads produced by emulsion polymerization may be enlarged by any known process for increasing the size of polymer beads. For example, polymer beads may be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably $C_{4-20}$ alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads may be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above together with or without a water miscible solvent for the crosslinking monomer. Suitable solvents include acetone, tetrahydrofuran (THF), methanol and dioxane. The resulting mixture is heated for about 1–12 hours, preferably about 4–8 hours at a temperature below the initiation temperature of the polymerization initiator, generally about 10°–80° C., preferably 30°–60° C. Optionally, the temperature of the mixture may be increased by 10–20% and the mixture heated for an additional 1–4 hours. The ratio of monomer to polymerization initiator is at least 100:1, preferably about 100:1 to about 500:1, more preferably about 200:1 in order to ensure a degree of polymerization of at least 200. Beads having this degree of polymerization are sufficiently pressure stable to be used in high pressure liquid chromatography (HPLC) applications. This thermal swelling process allows one to increase the size of the bead by about 110–160% to obtain polymer beads having an average diameter up to about 5 microns, preferably about 2–3 microns. The thermal swelling procedure may, therefore, be used to produce smaller particle sizes previously accessible only by the activated swelling procedure.

Following thermal enlargement, excess crosslinking monomer is removed and the particles are polymerized by exposure to ultraviolet light or heat. Polymerization may be conducted, for example, by heating the enlarged particles to the activation temperature of the polymerization initiator and continuing polymerization until the desired degree of polymerization has been achieved. Continued heating and polymerization allows one to obtain beads having a degree of polymerization greater than 500. The pore size of beads prepared by this process is less than 30 angstroms.

In the present invention, the packing material produced by Huber et al or U.S. Pat. No. 4,563,510 is modified and made generally applicable not only to RPIPC of short nucleic acid fragments, but also to fragments of any conceivable length, through alkylation of the polymeric beads with alkyl chains having more than two carbon atoms (longer than ethyl). The beneficial effects of alkylation are surprising to any expert in the field of DNA separations.

Employment of fully porous alkylated polystyrene beads was described originally by Morgan and Celebuski (R. L. Morgan and J. E. Celebuski, J. Chromatogr. (1991), 536:84–93). These authors found a solution to the problem of incomplete elution of fluorescein or biotin tagged nucleic acids from unmodified, fully porous poly-(styrene-divinylbenzene) beads (PRP-1 column, Hamilton Corp., Reno, Nev.). Following large injections for preparative scale separations, the tagged nucleic acids could not be eluted completely from the column and could be observed to elute as ghost peaks in the subsequent separations. This undesirable behavior was corrected by a switch to another type of fully porous Poly-(styrene-divinylbenzene) beads, which were modified with octadecyl substituents (Polyspher RP-18, EM Science, Cherry Hill, N.J., U.S.A.), In so doing, however, only the elution behavior could be improved, the resolution of the eluted peaks remained rather poor.

The work by Huber et al points away from the subject matter of the present invention because the first improvement of resolution in the separation of nucleic acids was accomplished by incorporation of polyvinyl alcohol into the polymer beads. Such a beneficial effect was interpreted by the authors as due to the presence of polar hydroxyl groups at, and close to the surface of the polymeric beads. The greatly improved resolution and efficiency of separation of all types of nucleic acids on beads modified with nonpolar substituents such as octadecyl groups in the present invention was therefore highly surprising.

The nonporous polymer beads of the present invention are alkylated by contacting the beads with an alkylating agent, such as an alkyl halide having greater than 2 carbon atoms. Suitable alkyl halides are straight-chain or branched alkyl chlorides, bromides and iodides containing at least three carbon atoms, preferably three to about 22 carbon atoms, more preferably about 8–18 carbon atoms. Alkylation is achieved by mixing the nonporous polymer beads with the alkyl halide in the presence of a Friedel-Crafts catalyst to effect electrophilic aromatic substitution on the aromatic rings at the surface of the polymer blend. Suitable Friedel-Crafts catalysts are well known in the art and include Lewis acids such as aluminum chloride, boron trifluoride, tin tetrachloride, etc. Alkylation of the nonporous polymer beads reduces the undesired adsorption of aromatic bases to the surface of the polymeric beads by shielding the aromatic moieties at the surface of the polymer bead. The reduced adsorption of aromatic bases improves the separation efficiency of the present method.

Alkylation may be accomplished by a number of known synthesis procedures. These include Friedel-Crafts alkylation with an alkyl halide, attachment of an alkyl alcohol to a chloromethylated bead to form an ether, etc. Although the preferred method for alkylating the nonporous polymer beads of the present invention is alkylation after the polymer bead has been formed, an alternative method of alkylation is to polymerize alkylated monomers to obtain an alkylated polymer bead. In this embodiment, the monomers will be substituted with alkyl groups having at least three carbon atoms, preferably 3–22 carbon atoms, more preferably 8–18 carbon atoms to provide an alkylated polymer bead.

As used herein, the term "nonporous" means a polymer bead having surface pores of less than 30 Å diameter as measured using a mercury porosity measurement method. Nitrogen adsorption (BET) measurements on the nonporous beads prepared in this invention had surface areas roughly two times the theoretical surface area. Preferably, the nonporous beads of the invention have a surface area of about 6–30, preferably about 10–20 m$^2$/gram as determined by nitrogen adsorption.

The improvements in RPIPC by the present invention open the possibility, for the first time, of a broad application of this methodology in the clinical diagnosis of oncogenes and viral genes. In current clinical practice, assays for viral genes are usually carried out using polymerase chain reaction (PCR) products and slab gel electrophoresis (SGE). SGE is a rather laborious procedure consisting of many labor intensive steps that are inaccessible to automation. A protocol for gene assays is described in N. C. Stellwagen Adv. Electrophoresis, (1987), 1:177–228, incorporated herein by reference.

Chromatographic separations of PCR products were first reported by Katz et al (E. D. Katz, L. A. Haff and R. Eksteen, J. Chromatogr., (1990), 512:433–444). The methodology employed by Katz et al (anion exchange HPLC or AEHPLC shows not only the disadvantages of low resolution that were discussed above, but it also exhibits slowly rising baselines due to ionic impurities eluting slowly from the PCR samples and through the column. These drawbacks, together with excessively long run times, have prevented the practical utilization of AEHPLC for clinical diagnosis.

The present invention thus makes possible a time efficient diagnostic assay for the detection of malignant tumors and/or viral illnesses in human or animal organisms by the separation and identification of nucleic acids which are characteristic markers of these diseases. The separation method of the invention is directly applicable to oncogenes or viral genes that have been amplified with the help of known PCR techniques. The separation methodology of the invention enables the efficient separation and quantitative determination of PCR products based on RPIPC performed using columns packed with the alkylated nonporous polymeric beads of the invention.

The preparation method of the invention is generally applicable to the chromatographic separation of single strand and double strand nucleic acids. In a preferred embodiment, the separation is by RPIPC. Also within the scope of the invention is the use of the alkylated nonporous beads in solid phase extraction procedures.

In a particular preferred embodiment, the polymer beads are nonporous, spherical poly(ethylvinylbenzene-divinyl benzene) beads produced in a two step process yielding a narrow distribution of particle sizes. In the first of these two steps, styrene is emulsion polymerized to form polystyrene seed particles having a mean diameter of about 0.8–3 microns, more preferably 1.5–2 microns. In the second step of the procedure, the polystyrene seed particles are contacted with a mixture of monovinyl and divinyl monomers (i.e., ethylvinylbenzene and divinylbenzene) and allowed to swell up to a size of 1–10 microns. Subsequent stepwise temperature increases in the reaction mixture lead to polymerization. The stepwise rather than sudden change of temperature helps to avoid agglomeration of the beads which are generally spherical in shape.

In RPIPC, the nucleic acids are paired with an ion pairing agent and then subjected to reverse phase chromatography using the alkylated beads of the present invention. The identity of the ion pairing agent is not critical and conventional ion pairing agents capable of forming ion pairs with nucleic acids may be used in the present invention. Typical ion pairing agents include trialkylammonium salts of organic or inorganic acids, for example tetramethyl, tetraethyl, tetrapropyl and tetrabutyl ammonium acetates, halides, etc. A particularly preferred ion pairing agent is tetraethylammonium acetate (TEAA).

To achieve high resolution chromatographic separations of nucleic acids, it is generally necessary to tightly pack the chromatographic column with the solid phase polymer beads. Any known method of packing the column with a column packing material may be used in the present invention to obtain adequate high resolution separations. Typically, a slurry of the alkylated polymer beads is prepared using a solvent having a density equal to or less than the density of the polymer beads. The column is then filled with the polymer bead slurry and vibrated or agitated to improve the packing density of the polymer beads in the column. Mechanical vibration or sonification are typically used to improve packing density.

For example, to pack a 50×4.6 mm i.d. column, 1.4 g of alkylated beads may be suspended in 15 ml tetrahydrofuran with the help of sonication. The suspension is then packed into the column using 50 ml methanol at 70 MPa of pressure. In the final step, the packed bed is washed with 50 ml deionized water. This reduces the swelling of beads and improves the density of the packed bed.

Other features of the invention will become apparent in the course of the following descriptions of exemplary embodiments which are given for illustration of the invention and are not intended to be limiting thereof.

EXAMPLES

Example 1

Sodium chloride (0.236 g) was added to 354 ml deionized water in a reactor having a volume of 1.0 liter. The reactor was equipped with a mechanical stirrer, reflux condenser and a gas introduction tube. The dissolution of the sodium chloride was carried out under inert atmosphere (argon), assisted by stirring (350 rpm) and at an elevated temperature (87° C.) Freshly distilled styrene (33.7 g) and 0.2184 g potassium peroxodisulfate dissolved ($K_2S_2O_8$) in 50 ml deionized water were then added. Immediately after these additions, the gas introduction tube was pulled out of the solution and positioned above the liquid surface. The reaction mixture was subsequently stirred for 6.5 hours at 87° C. After this, the contents of the reactor were cooled down to ambient temperature and diluted to a volume yielding a concentration of 54.6 g of polymerized styrene in a 1000 ml volume of suspension resulting from the first step. The amount of polymerized styrene in 1000 ml was calculated to include the quantity of the polymer still sticking to the mechanical stirrer (approximately 5–10 g). The diameter of the spherical beads in the suspension was determined by light microscopy to be about 1.0 micron.

Beads resulting from the first step are still generally too small and also too soft (low pressure stability) for use as chromatographic packings. The softness of these beads is caused by an insufficient degree of crosslinking. In a second step, the beads are enlarged and the degree of crosslinking is increased. The protocol for the second step is based on the activated swelling method described by Ugelstad et al. (J. Ugelstad, P. C. Mork, K. Herder Kaggerud, T. Ellingsen and A. Berge, Adv. Colloid Interface Sci., (1980), 13:101–140). In order to initiate activated swelling or the second synthetic step, the aqueous suspension of polystyrene seeds (200 ml) from the first step was mixed first with 60 ml acetone and then with 60 ml of a 1-chlorododecane emulsion. To prepare the emulsion, 0.206 g sodium dodecylsulfate, 49.5 ml deionized water and 10.5 ml 1-chlorododecane were brought together and the resulting mixture was kept at 0° C. for 4 hours and mixed by sonication during that entire time period until a fine emulsion of <0.3 microns was obtained. The mixture of polystyrene seeds, acetone and 1-chlorododecane emulsion was stirred for about 12 hours at room temperature, during which time the swelling of beads occurred. Subsequently, the acetone was removed by a 30 minute distillation at 80° C. Following the removal of acetone, the swollen beads were further grown by the addition of a 310 g ethyldivinylbenzene and divinylbenzene (DVB) (1:1.71) mixture also containing 2.5 g dibenzoylperoxide as an initiator. The growing occurred with stirring and with occasional particle size measurements by means of light microscopy.

After completion of the swelling and growing stages, the reaction mixture was transferred into a separation funnel. In an unstirred solution, the excess amount of the monomer separated from the layer containing the suspension of the polymeric beads and could thus be easily removed. The remaining suspension of beads was returned to the reactor and subjected to a stepwise increase in temperature (63° C. for about 7 hours, 73° C. for about 2 hours and 83° C. for about 12 hours) leading to further increases in the degree of polymerization (>500). The pore size of beads prepared in this manner was below the detection limit of mercury porosimetry (<30Å).

After drying, the dried beads (10 g) from step two were suspended in 100 ml 1-chlorododecane and stirred (370 rpm) for 12 hours at 100° C. following an addition of 1 g of aluminum chloride. At the end of this period the reaction mixture was cooled down to 80° C. and mixed with 150 ml of 4M hydrochloric acid. After 2 minutes of stirring, the reaction mixture, now containing hydrochloric acid, was transferred into a separation funnel and overlayed by 300 ml of n-heptane. The phases were stirred into each other and after subsequent separation of phases, the aqueous phase was removed and discarded. The remaining organic phase was washed two additional times with 200 ml of 1M hydrochloric acid and subsequently centrifuged at 5000 rpm. The separated beads were washed four times with 100 ml n-heptane and then two times with each of the following: 100 ml diethylether, 100 ml dioxane and 100 ml methanol. Finally, the beads were dried.

Alternatively, the alkylation was carried out using tin chloride by means of a procedure which is otherwise similar to that utilizing aluminum chloride. 100 ml 1-chlorooctadecane, 10 g poly(styrene/ethylstyrene/divinylbenzene) beads and 5 ml $SnCl_4$ were stirred at 100° C. for 12 hours. The mixture was cooled to room temperature, 100 ml n-heptane was added and the mixture was then extracted with 4×300 ml water in a separation funnel. The centrifuging which followed was carried out for five minutes at 5000 rpm. The supernatant and 1-chlorooctadecane were discarded and water was removed as completely as possible. Washing with 2×150 ml n-heptane, 2×150 ml dioxane and with 2×150 ml methanol completed the procedure. Each one of the washing steps was followed by centrifugation at 5000 rpm. The alkylated beads were then dried at 60° C.

Alkylation of the aromatic rings of the polymer was verified by Fourier Transform Infrared spectroscopy (FTIR). The beads differed only slightly in size from each other. The mean value for the particle diameter was found to be 2.10 microns, with a standard deviation of 0.12 micron.

The separation of single and double stranded nucleic acids was accomplished using RPIPC. Triethylammonium acetate was used as the ion pairing agent. Elution was effected with the help of a linear organic solvent gradient of acetonitrile.

FIG. 1 shows the separation of DNA restriction fragments on the nonporous poly(ethylvinylbenzene-divinylbenzene) beads prepared as described above. The chromatographic conditions were as follows: Column 50×4.6 cm i.d. Mobile phase: 0.1M TEAA, pH 7.0. Gradient: 7.5–13.75% acetonitrile in 4 minutes, followed by 13.75–16.25% acetonitrile in 6 minutes. Flow rate: 1 ml/min. Column temperature: 50° C. Detection: UV at 254 nm. Sample: 0.5 µg pBR322 DNA-Hae III restriction digest.

FIG. 1(a) shows a separation with unmodified beads; FIG. 1(b) shows a separation with beads modified with polyvinyl alcohol according to the procedure by Huber et al. FIG. 1(c) shows results carried out on alkylated beads made by the synthetic procedure described above. Only the last of the three chromatograms, FIG. 1(c), shows a clean characterization of fragments, related to the number of bases over a broad range of fragment lengths. For shorter fragment lengths, as shown by the FIG. 1(b), the polyvinyl alcohol modified beads possess a degree of utility, showing improved resolution over that in FIG. 1(a).

Example 2

Seed polystyrene latex was prepared using 0.374 g NaCl, 0.1638 $K_2S_2O_8$, 404 ml water, 37 ml styrene was stirred at 81° C. at 350 rpm for 6 hours. The resulting seed particles had a diameter of 1.3 microns. Then, 200 ml of the seed latex was swollen with a mixture of 50 ml divinylbenzene, 0.5 dibenzoylperoxide, and 5 ml acetone. The mixture was stirred for 6 hours at 40° C. and 1 hour at 45° C. The final diameter of the particles was 1.8 microns. Next, the excess divinylbenzene was removed and the particles polymerized for 12 hours at 65° C. followed by 14 hours at 85° C.

Example 3

2.0 micron seed polystyrene was prepared using 0.374 NaCl K$_2$S$_2$O$_8$, 404 ml water, 37 ml styrene was stirred at 71° C. at 350 rpm for 12 hours. The resulting seed particles were 2.0 micron. After swelling and polymerization, the final nonporous beads product was 2.8 microns. The final product was washed and alkylated with 1 chlorooctadecane using the synthesis method conditions described previously. A 4.6×50 mm column packed with these particles was used to separate DNA fragments.

Example 4

Figure 2:
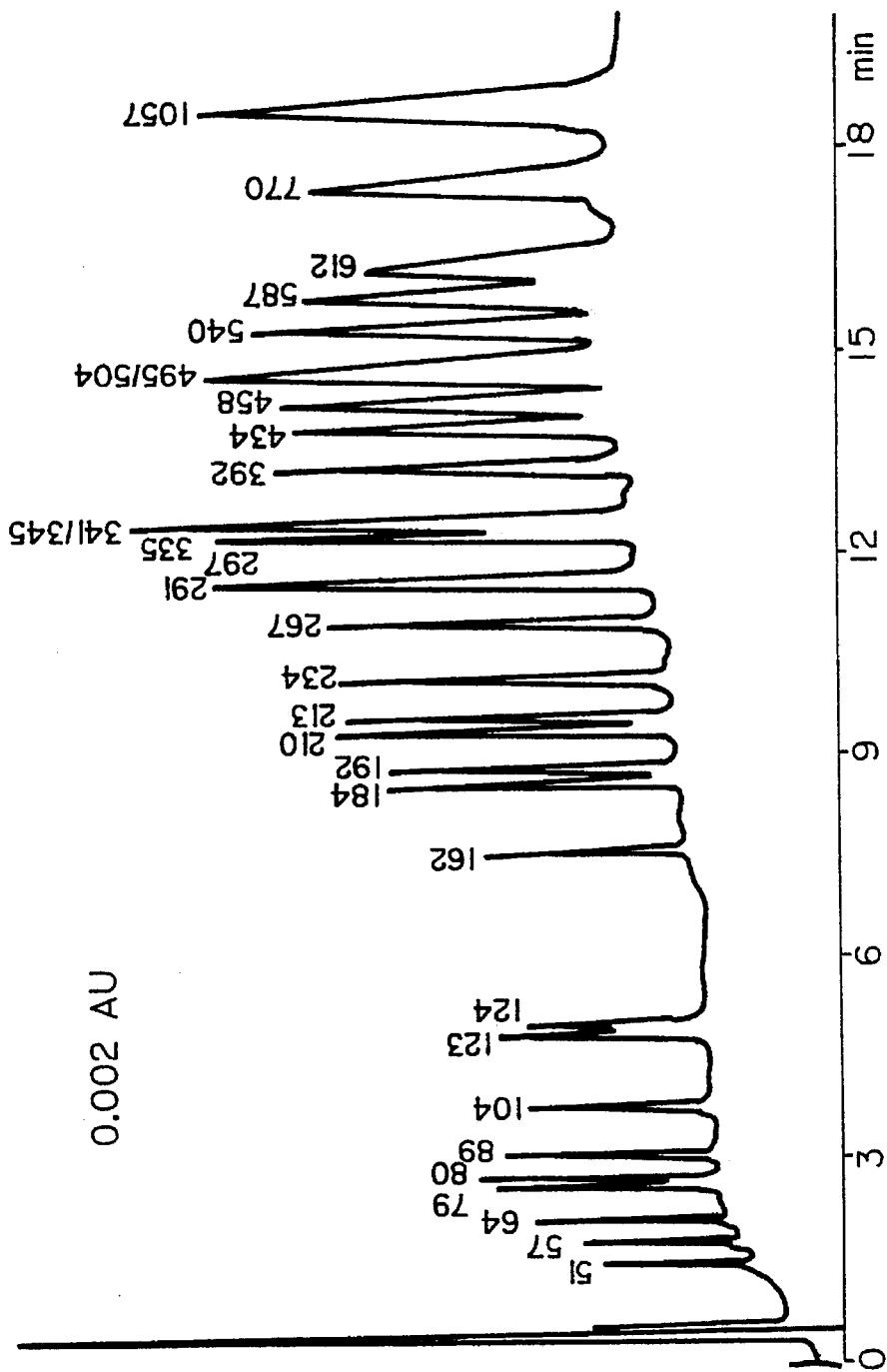
FIG. 2 is a chromatogram showing the high resolution separation of DNA restriction fragments according to Example 5.

FIG. 2 shows the high resolution separation of DNA restriction fragments using octadecyl modified, nonporous poly(ethylvinylbenzene-divinylbenzene)beads- The experiment was conducted under the following conditions: Column: 50×46 mm i.d. Mobile phase: 0.1 M TEAA, pH 7.0. Gradient: 8.75–11.25% acetonitrile in 2 minutes, followed by 11.25–14.25% acetonitrile in 10 minutes, 14.5–15.25% acetonitrile in 4 minutes, and by 15.25–16.25% acetonitrile in 4 minutes. Flow rate: 1 ml/min. Column temperature: 50° C. Detection: UV at 254 nm. Sample: Mixture of 0.75 µg p BR322 DNA-Hae III restriction digest and 0.65 µg Φ×174 DNA Hinc II restriction digest.

In addition to the use of the discussed stationary phase, the high resolution shown in FIG. 2 was obtained by optimizing the concentration of triethylammonium acetate (TEAA), shape of the gradient curve, column temperature and flow rate. As far as the concentration of triethylammonium acetate is concerned, the resolution of peaks was continuously enhanced in going from 25 mM to at least 125 mM of TEAA. The gradient was optimized by decreasing the steepness of gradient curve with increasing fragment lengths of DNA molecules. The best separations of DNA molecules are accomplished at about 30°–50° C. Denaturation of DNA at higher than about 50° C. prevents utilization of higher column temperatures for double stranded DNA fragments.

Example 5

If the gradient delay volume is minimized, the separation of PCR products and hybrid nucleic acids derived from various sources of nucleic acids including living and dead organisms (animal and plant), as well as parts of such organisms (e.g. blood cells biopsies, sperm, etc.) on octadecyl modified, nonporous poly-(ethylvinylbenzene-divinylbenzene)beads can be achieved with run times under 2 minutes.

The analysis of PCR products and hybrid nucleic acids usually requires only separation and detection of one or two species of known length. Because of this, the resolution requirements are considerably less severe than for separations of DNA restriction fragments. Such less stringent resolution requirements allow the utilization of steep gradients and consequently lead to still shorter run times. The recovery rate for a DNA fragment containing 404 base pairs was about 97.5%.

Unlike capillary electrophoresis (CE), PCR samples do not have to be desalted prior to analysis of RPIPC. This represents a decisive advantage of RPIPC over CE. With RPIPC, it is thus possible to achieve a fully automated analysis of PCR samples, if an automatic autosampler is utilized. Moreover, since the volume of sample injection is known, in contrast to CE, quantitation over several orders of magnitude can be achieved without the need for an internal standard, hence allowing the quantitation of gene expression as well as the determination of virus titers in tissues and body fluids. A fully automated version of the method of the invention has been used to discriminate (distinguish) normal from mutated genes as well as to detect oncogenes, bacterial and viral genome nucleic acids (hepatitis C virus, HIV, tuberculosis) for diagnostic purposes. Moreover, adjustment of column temperature allows one to modulate the stringency of hybridization reactions.

Figure 3:
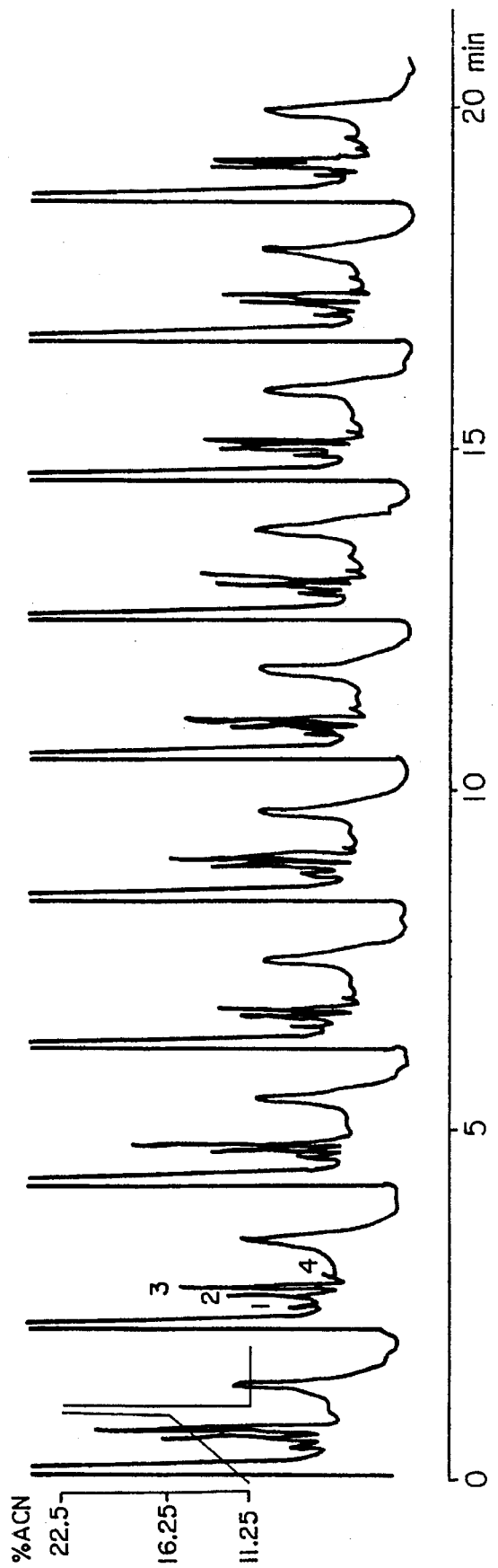
FIG. 3 is a chromatogram showing the rapid repetitive separation and analysis of PCR products according to Example 3.

The suitability of the modified polymer beads of the invention for clinical use is obvious from FIG. 3. FIG. 3 documents an experiment conducted under the following conditions: Column: 50×46 mm i.d. Mobile phase: 0.1M TEAA, pH 7.0. Gradient: 11.25–13.75% acetonitrile in 1 minute, followed by 22.5% acetonitrile for 6 seconds and 11.25% acetonitrile for 54 seconds. Flow rate: 3 ml/min. Column temperature: 50° C. Detection: UV at 256 nm. Sample: 20 µl of a PCR sample. In FIG. 3, 1=unspecific PCR product, 2=PCR product having 120 base pairs, 3=PCR product with 132 base pairs and 4=PCR product with 167 base pairs.

PCR methods and processes are described in R. K. Saiki et al, Science, (1985), 230:1350–1354 and K. B. Mullis in U.S. Pat. No. 4,683,202. These references are incorporated herein by reference for a more complete description of methods and processes for obtaining PCR samples which can be separated using the method of the present invention.

As illustrated, the repetitive analysis of PCR products is highly reproducible under the described analytical conditions. Especially important is the observation, that the results are not in any way influenced by the preceding injection. This finding represents additional evidence of the suitability the present method for routine use under real conditions in clinical laboratories.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for separating a mixture of nucleic acids, comprising
   flowing a mixture of nucleic acids having up to 1000 base pairs through a separation column containing polymer beads having a pore diameter less than 30 Å as measured by mercury porosity, alkylated with alkyl groups having 3–22 carbon atoms sufficient to reduce adsorption of nucleic acid bases to said beads, and having an average diameter of 1–100 microns, and
   separating said mixture of nucleic acids.

2. The method of claim 1, wherein said separation is by ion pair reverse phase chromatography.

3. The method of claim 2, wherein said polymer beads have an average diameter of about 1–5 microns.

4. The method of claim 1, wherein said polymer beads are comprised of a copolymer of vinyl aromatic monomers.

5. The method of claim 4, wherein said vinyl aromatic monomers are selected from the group consisting of styrene, alkyl substituted styrene, alpha-methylstyrene and alkyl substituted alpha-methylstyrene.

6. The method of claim 1, wherein said polymer beads are comprised of a copolymer of styrene, C$_{1-6}$ alkyl-vinyl benzene and divinylbenzene.

7. The method of claim 1, wherein said polymer beads further contain polyvinyl alcohol.

8. The method of claim 1, wherein said alkyl groups contain 8–18 carbon atoms.

9. The method of claim 1, wherein said nucleic acids have about 200–600 bases or base pairs.

10. The method of claim 9, wherein said nucleic acids have about 20–80 bases or base pairs.

11. The method of claim 1, wherein said nucleic acids are RNA.

12. The method of claim 1, wherein said nucleic acids are DNA.

13. The method of claim 1, wherein said alkylated nonporous beads have a surface are of 6–30 m$^2$/gram as determined by nitrogen adsorption.

14. The method of claim 1, wherein said mixture of nucleic acids is a polymerase chain reaction product.

15. A method for detecting the occurrence of a tumor or virus which expresses a characteristic nucleic acid having a known length of up to 1000 base pairs in an organism, comprising the steps of:

sampling an organism to obtain a sample of said expressed nucleic acid, producing a polymerase chain reaction product containing multiple copies of said expressed nucleic acid, separating the nucleic acids in said polymerase chain reaction product by contacting said polymerase chain reaction product with a separation column containing polymer beads having a pore diameter less than 30 Å as measured by mercury porosity, alkylated with alkyl groups having 3–22 carbon atoms sufficient to reduce adsorption of nucleic acid bases to said beads, and having an average diameter of 1–100 microns, and detecting said expressed nucleic acid in said separated polymerase chain reaction product.

16. The method of claim 15, wherein said separation is by ion pair reverse phase chromatography.

17. The method of claim 15, wherein said polymer beads have an average diameter of about 1–5 microns.

18. The method of claim 15, wherein said polymer beads are comprised of a copolymer of vinyl aromatic monomers.

19. The method of claim 18, wherein said vinyl aromatic monomers are selected from the group consisting of styrene, alkyl substituted styrene, alpha-methylstyrene and alkyl substituted alpha-methylstyrene.

20. The method of claim 15, wherein said polymer beads are comprised of a copolymer of styrene, C$_{1-6}$ alkyl-vinyl benzene and divinyl benzene.

21. The method of claim 15, wherein said polymer beads further contain polyvinyl alcohol.

22. The method of claim 15, wherein said alkyl groups contain 8–18 carbon atoms.

23. The method of claim 15, wherein said nucleic acids have about 200–600 bases or base pairs.

24. The method of claim 15, wherein said nucleic acids have about 20–80 bases or base pairs.

25. The method of claim 15, wherein said nucleic acids are RNA.

26. The method of claim 15, wherein said nucleic acids are DNA.

27. The method of claim 15, wherein said alkylated nonporous beads have a surface are of 6–30 m$^2$/gram as determined by nitrogen adsorption.

28. A polymeric bead having a pore diameter less than 30 Å as measured by mercury porosity, alkylated with alkyl groups having 3–22 carbon atoms sufficient to reduce adsorption of nucleic acid bases to said beads, having an average bead diameter of 1–100 microns, and a surface area of 6–30 m$^2$/gram as determined by nitrogen adsorption.

29. The polymer bead of claim 28, wherein said polymer beads have an average diameter of about 1–10 microns.

30. The polymer bead of claim 28, wherein said polymer beads have an average diameter of about 1–5 microns.

31. The polymer bead of claim 28, wherein said polymer beads are comprised of a copolymer of vinyl aromatic monomers.

32. The polymer bead of claim 28, wherein said vinyl aromatic monomers are selected from the group consisting of styrene, alkyl substituted styrene, alpha-methylstyrene and alkyl substituted alpha-methylstyrene.

33. The polymer bead of claim 28, wherein said polymer beads are comprised of a copolymer of styrene, C$_{1-6}$ alkyl-vinyl benzene and divinyl benzene.

34. The polymer bead of claim 28, wherein said polymer beads further contain polyvinyl alcohol.

35. The polymer bead of claim 28, wherein said alkyl groups contain 8–18 carbon atoms.

\* \* \* \* \*